United States Patent [19]
Reitz

[11] Patent Number: 5,449,290
[45] Date of Patent: Sep. 12, 1995

[54] DENTAL MIRROR INCORPORATING AIR FLOW

[76] Inventor: Georg Reitz, 3 Caroline St., Burlington, Mass. 01803

[21] Appl. No.: 265,744

[22] Filed: Jun. 27, 1994

[51] Int. Cl.⁶ .................... A61C 1/00; A61C 3/00; A61B 1/24
[52] U.S. Cl. ............................................ 433/31; 433/30
[58] Field of Search .................. 433/30, 31, 80, 91; 128/21, 22

[56] References Cited

U.S. PATENT DOCUMENTS

| | | | |
|---|---|---|---|
| 1,925,981 | 9/1933 | Hopkins | 433/31 |
| 3,092,910 | 6/1963 | Warriner | 433/31 |
| 4,279,594 | 7/1981 | Rigutto | 433/31 |
| 4,400,157 | 8/1983 | Moore | 433/31 |
| 4,629,425 | 12/1986 | Detsch | 433/31 |
| 4,925,391 | 5/1990 | Berlin | 433/31 |
| 5,139,420 | 8/1992 | Walker | 433/31 |
| 5,295,826 | 3/1994 | Yandell et al. | 433/31 |

FOREIGN PATENT DOCUMENTS 3725243  2/1989  Germany .................. 433/31

*Primary Examiner*—Nicholas D. Lucchesi
*Attorney, Agent, or Firm*—Michael I. Kroll

[57] ABSTRACT

A dental mirror has an airflow bore extending therethrough. There is an airflow aperture proximate the mirror surface to prevent fogging and debris buildup. The airflow is provided and controlled by the standard compressed air outlet available in most dental offices. The mirror section and handle section are threadably engaged to one another to allow for disassembly prior to sterilization between procedures.

1 Claim, 1 Drawing Sheet

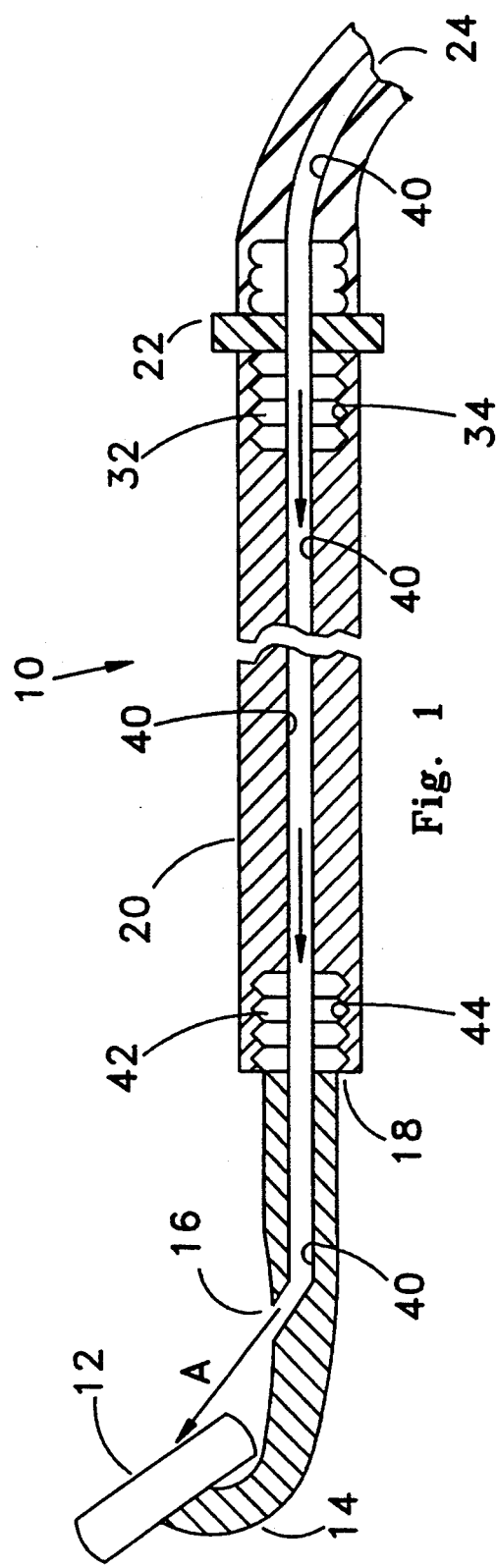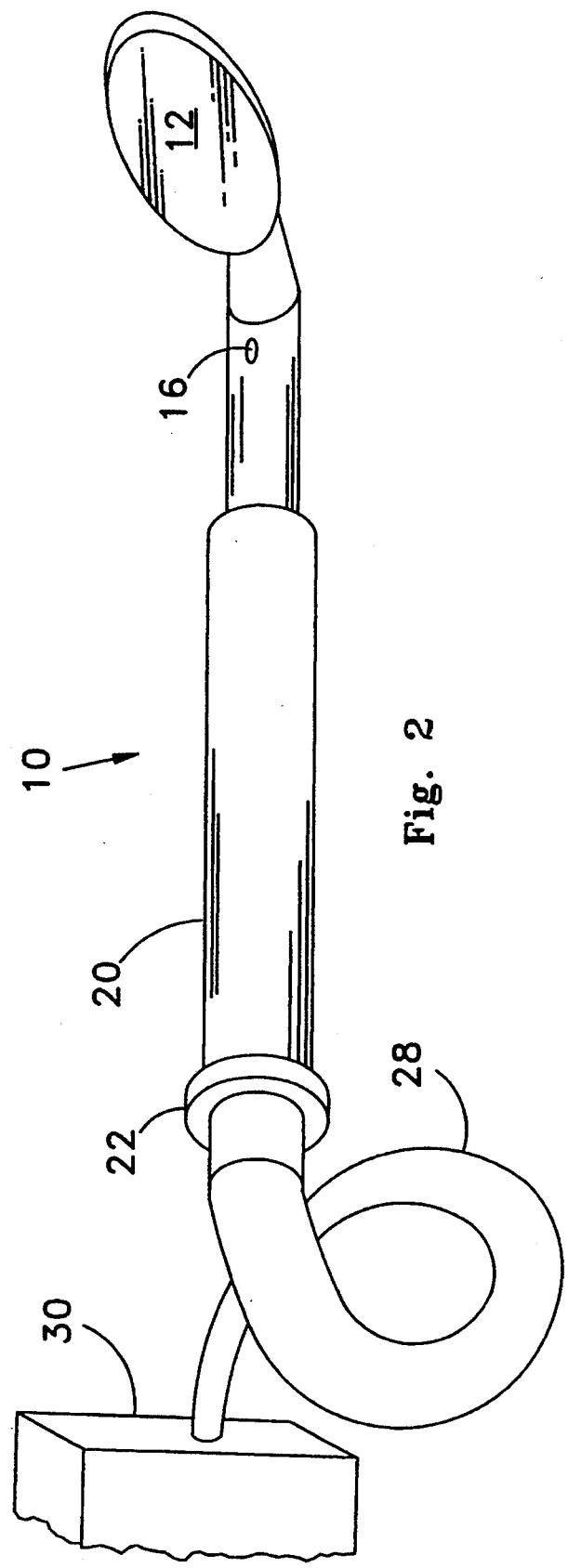

DENTAL MIRROR INCORPORATING AIR FLOW

BACKGROUND OF THE INVENTION

REFERENCE TO RELATED PUBLICATIONS

The present invention was registered in the United States Patent and Trademark Office under the Document Disclosure Program. The date received was May 20, 1993 and the registration number is 331,496.

1. Field of the Invention

The present invention relates to dental mirrors. More specifically, it relates to a dental mirror having a bore therein to direct an airflow onto the surface of the mirror to dissipate mist or debris generated inside the patient's mouth during a procedure. Even more specifically, it relates to a dental mirror with an airflow bore therein, that consists of threadably engaged mirror and handle sections, to allow for cleaning and sterilization of the instrument.

2. Description of the Prior Art

During dental procedures that involve obscured or difficult to reach places within the mouth, handheld mirrors are used to view the area being worked on. When drilling is involved, the cooling and lubricating fluid sprayed from the drill can fog the mirror. Additionally, saliva and tooth debris can cloud the practitioner's view. This entails the dentist to cease work and clean the mirror, slowing the procedure and subjecting the patient to a more protracted period of time in the office. The present invention seeks to overcome the limitations of present dental mirrors by providing a bore within its body to allow for a flow of air to be directed onto the reflective surface of the mirror, thus blowing away debris and defogging the surface. The present invention also is provided with cooperating threaded members, allowing the tool to be disassembled for easier cleaning and sterilization between procedures.

A number of relevant U.S. patents were uncovered during a search in this art area and are discussed hereinafter:

First is U.S. Pat. No. 3,092,910 issued on Jun. 11, 1963 to Joe F. Warriner. This discloses an end instrument for a dental evacuator wherein a fluid flow is directed onto and across the surface of the mirror through an inlet passage, and then is taken up into a separate outlet passage. Both the inlet and outlet passage are contained within an elongate handle portion of the device.

In U.S. Pat. No. 4,279,594 issued on Jul. 21, 1991 to Martin A. Rigguto there is disclosed a dental hand mirror wherein a hollow handle portion is attached to a mirror at one end and where a flow of air is directed through the handle and onto and across the surface of the mirror.

Another patent of interest is U.S. Pat. No. 4,925,391 issued on May 15, 1990 to Göran Berlin. In this document there is disclosed a dental instrument wherein a mirror portion is firmly attached to a handle portion that includes a first internal channel connected to a suction source and a second internal channel having one end open proximate the mirror portion, and where the second channel is connected to a pressurized air source so that air is blown over the surface of the mirror.

Lastly, U.S. Pat. No. 5,139,420 issued on Aug. 18, 1992 to William S. Walker discloses a dental mirror system where a fluid conduit provides a stream of fluid across the surface of the mirror to remove deposited matter from the surface thereof.

While some of these patents have overcome some of the problems noted above, they do not overcome all of the problems, and further, fall short in meeting the needs of skilled dentists who are seeking a practical and economical dental mirror which is fog free and sterilized easily.

None of the above inventions and patents, taken either singly or in combination, is seen to describe the instant invention as claimed.

SUMMARY OF THE INVENTION

The present invention is a dental mirror having an airflow bore extending therethrough, with an aperture proximate the mirror surface to prevent fogging and debris buildup. The airflow is provided and controlled by the standard compressed air outlet available in most dental offices. The mirror section and handle section are threadably engaged to one another to allow for disassembly before sterilization and cleaning between procedures.

Accordingly, it is a principle object of the invention to provide a dental mirror that incorporates an airflow across the surface of the mirror to prevent fogging or debris buildup.

It is another object of the invention to provide a dental mirror incorporating an airflow where the mirror portion and handle portion of the device are threadably connected to one another, thus allowing the user to easily disassemble and sterilize the device between uses.

It is a further object of the invention to provide a dental mirror where the incorporated airflow is provided and controlled by the existing compressed air outlet standard in most dental offices.

It is a general goal of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

The present invention meets or exceeds all the above objects and goals. Upon further study of the specification and appended claims, further objects and advantages of this invention will become apparent to those skilled in the art.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is a cutaway view of the present invention showing the airflow bore and location of the threaded engagements between separate portions of the device.

FIG. 2 is a perspective view of the present invention.

DETAILED DESCRIPTION OF THE PREFERRED EMBODIMENT

The present invention is indicated in the drawing figures generally at 10. The device 10 has three main sections; airflow receiving portion 22, grip portion 20, and mirror support portion 18.

The first section to be discussed will be the airflow tube receiving portion 22. This portion includes a threaded engagement area 32 that cooperates with a threaded bore 34 in the grip portion 20 of the device. The cooperating threaded portions 32, 34 are shown clearly in FIG. 1. Extending from the airflow receiving portion 22 to the airflow source 30 is a flexible tube 28 that delivers the air to the airflow inlet 24. The airflow source 30 is a standard compressed air source as is found in most dental offices for powering drills and the like. The tube 28 would be of sufficient length to allow for the placement and manipulation of the device 10 within and around the patient's oral cavity. It is contemplated that the device could also include a foot pedal (not shown) or other type of controllable valve to vary the velocity of the airflow at the user's discretion.

The grip portion 20 of the device 10 is preferably a generally cylindrical tube with the airflow bore 40 extending through it. At the distal end of the grip portion 20 in relation to the airflow receiving portion 22 is the mirror support portion 18. This is connected to the grip portion 20 by a threaded member 42 that cooperates with the threaded bore 44 in the grip portion 20 of the device 10 as is seen in FIG. 1.

The mirror support portion 18 includes a "gooseneck" or angled area 14 proximate the mirror 12 and further includes an airflow aperture 16 that is configured to direct the flow of air onto and across the surface of the mirror 12 as is indicated by arrow A in FIG. 1.

Thus it is seen that the entire device 10 is able to be broken down into constituent parts 18, 20, 22 to allow for the cleaning and sterilization of the same between procedures. It is contemplated that the device 10 could be made of a stainless steel or other type of material that would be in accordance with the appropriate health and safety codes and would be able to withstand repeated exposure to the sterilization process without material degradation. It should also be mentioned that the threaded members 32, 42 and their cooperating threaded bores 34, 44 could be replaced by other types of removable engagement means such as a snap fit or a "push and twist" type of engagement; as long as the airflow bore 40 extends completely through all the portions allowing for fluid communication between the airflow inlet 24 and the outlet or aperture 16 proximate the mirror 12.

Following is a list of the elements described in the above specification:

| | |
|---|---|
| dental mirror apparatus | 10 |
| airflow tube receiving portion | 22 |
| airflow tube threaded member | 32 |
| airflow tube receiving bore | 34 |
| grip portion | 20 |
| flexible tube | 28 |
| airflow source | 30 |
| airflow inlet | 24 |
| airflow bore | 40 |
| mirror support portion | 18 |
| mirror support threaded member | 42 |
| mirror support receiving bore | 44 |
| angled area | 14 |
| mirror | 12 |
| airflow outlet aperture | 16 |
| directional arrow | A |

It is to be understood that the present invention is not limited to the sole embodiment described above, but encompasses any and all embodiments within the scope of the following claims.

I claim:

1. A dental mirror apparatus incorporating a directed airflow comprising:
    an airflow receiving portion;
    a grip portion;
    a mirror support portion supporting a reflective surface;
    means for facilitating the cleaning and sterilization of each of said portions separately comprising:
        a first detachable engagement means for threadable engagement between said airflow receiving portion and said grip portion, and
        a second detachable engagement means for threadable engagement between said mirror support portion and said grip portion;
    an airflow bore extending completely through said airflow receiving portion and said grip portion; and
    an airflow directional bore and aperture within said mirror support portion;
    said first and second engagement means holding said portions together to provide fluid communication between said airflow receiving portion, said grip portion, and said mirror support portion to direct an airflow onto and across said reflecting surface while at the same time permitting convenient disassembly for cleaning and sterilization of each said portion separately.

* * * * *